United States Patent [19]

Bliah

[11] Patent Number: 4,742,046
[45] Date of Patent: May 3, 1988

[54] METHODS AND COMPOSITIONS FOR INHIBITING THE INFECTIOUS ACTIVITY OF VIRUSES

[75] Inventor: Madeleine A. M. Bliah, Paris, France

[73] Assignee: Medisearch S.A., Zurich, Switzerland

[21] Appl. No.: 749,936

[22] Filed: Jun. 27, 1985

Related U.S. Application Data

[63] Continuation-in-part of Ser. No. 637,421, Aug. 3, 1984, abandoned.

[51] Int. Cl.[4] .............. A61K 37/02; A61K 35/78; C07K 15/14
[52] U.S. Cl. .................. 514/8; 424/195.1; 514/888; 530/370
[58] Field of Search ............ 514/8, 888; 530/370; 424/195.1

[56] References Cited

U.S. PATENT DOCUMENTS 4,421,746  12/1983  Kojima et al. .............. 514/889
4,440,761  4/1984  Kojima et al. .............. 514/889

OTHER PUBLICATIONS

Paulo, cited in Biological Abstracts, vol. 63, 1977, No. 7138.
Broekaert et al., Biochem. J., (1984), 221, pp. 163–169.

Primary Examiner—J. R. Brown
Assistant Examiner—Jacqueline M. Stone
Attorney, Agent, or Firm—Ladas & Parry

[57] ABSTRACT

Diseases of animals and man caused by enveloped viruses can be inhibited by the use of non-toxic lectins. Suitable compositions and methods of administration of such lectins are described.

21 Claims, No Drawings

METHODS AND COMPOSITIONS FOR INHIBITING THE INFECTIOUS ACTIVITY OF VIRUSES

RELATED APPLICATION

This is a continuation-in-part of my copending application No. 637,421 filed on Aug. 3, 1984, now abandoned.

BACKGROUND OF THE INVENTION

The present invention relates to methods and compositions for inhibiting the infectious activity of viruses by the use of lectins. More specifically, it relates to the use of lectins obtained from *Sambucus nigra* for inhibiting the activity of enveloped viruses.

Viruses may be classified in a number of different ways. However, one major division is between those viruses wherein the virion comprises an envelope surrounding the nucleocapsid and those which do not. Among the viruses wherein the nucleocapsid is enveloped are: (1) DNA viruses such as Herpesviridae including herpes simplex, cytomegalovirus, varicella zoster, Epstein Barr and other viruses affecting horses, chickens and cows; Poxviridiae including smallpox, vaccinia, human monkeypox, sheep, bird, swine pox viruses and Iridoviridae; (2) RNA viruses such as Togaviridae including alphaviruses such as Sindbis, equine and encephalitis viruses: flaviviruses such as Yellow fever and dengue viruses; rubiviruses such as rubella and pestiviruses; Arenaviridae, Orthomyxoviridae, including influenza types A, B and C viruses; Paramyxoviridae such as parainfluenza (types 1, 2, 3 and 4); respiratory syncitial, mumps, measles and Newcastle disease viruses; Coronaviridae such as coronavirus; Rhabdoviridae; Retroviridae such as oncovirinae, spumavirinae and lentivirinae; Bunyaviridae such as bunyavirus; and certain unclassified viruses such as hepatitis A, hepatitis B, non A non B heptatis viruses, as well as certain viruses connected with tumor production and disorders such as acquired immune deficiency syndrome.

Enveloped animal viruses are characterized by the presence of a membrane consisting of a lipid bilayer with glycoprotein projections, or spikes, on the outer surface of the viral envelope. These spikes consist of virus-coded glycoprotein molecules which are essential for viral infectivity and replication. The antigenic specificity of the virus is also determined by these molecules.

The viral glycoproteins are involved in the early interactions between the virion and the cell, i.e. adsorption to the cell surface and penetration of the virion into the cell. The exact sequence of events in the penetration of enveloped viruses into cells is still not clear. However, in the case of the paramyxo- and myxoviruses, it is clear that fusion of viral and cell membranes is involved in the penetration step and that penetration is mediated by a viral glycoprotein. Specific cleavage of the viral glycoprotein activates the ability of the virus to initiate infection.

Lectins are a group of proteins capable of binding specifically to carbohydrate moieties on various cell surfaces. The interaction of a few lectins with glycoproteins on virus envelope has been investigated. It has been found that Concanavalin A and *Ricinus communis agglutinin*, especially the former, do interfere with the activity of a number of viruses. The toxicity of Concanavalin A and *Ricinus communis agglutinin*, however, precludes their clinical use (the latter is one of the most toxic substances known). Other less toxic lectins have been investigated with mixed results.

The ability of Concanavalin A to interfere with viruses has been described in many articles in the literature. For example, Calafat and Hageman in J. Gen. Virol 14: 103–106 (1972) describe the binding of murine RNA tumor viruses with Concanavalin A. Birdwell and Strauss in J. Virol. 11: 502–507 (1973) reported that Concanavalin A and *Ricinus communis agglutinin* agglutinate Sindbis virus. Stewart et al. in Proc. Nat. Acad. Sci. USA 70: 1308–1312 (1973) describe the use of Concanavalin A to selectively agglutinate murine and avian oncornavirions, especially Friend virus. Okado and Kim in Virol. 50: 507–515 (1972) showed that the activity of the enveloped viruses of Sendai virus and herpes simplex virus was destroyed by Concanavalin A, but that this lectin had no effect on unenveloped polio virus.

Ito and Barron in J. Virol. 13: 1312–1318 (1974) report that whereas Concanavalin A inhibited the infectivity of herpes simplex virus type 1, phytohaemaglutinin-P. wheat germ agglutinin and pokeweed mitogen had no such effect. They also reported that Concanavalin A inactivated herpes simplex virus type 2, pseudorabies virus and vesicular stomatitis virus, but that there was no such effect on vaccinia, simian adenovirus SV 15 and echovirus type 6. The data suggested that Concanavalin A blocked the binding sites on the virion envelope.

Ito and Barron in J. Gen. Virol. 33: 259–266 (1976) showed that while phytohaemagglutinin-P failed to inactivate herpes simplex virus, it did enhance the inactivation effected by Concanavalin A.

Finkelstein and McWilliams in Virol. 69 570–586 (1976) reported the effects of a variety of lectins on various viruses. In particular, they reported that phytohaemagglutinin-P, Concanavalin A, *Ricinus communis agglutinin* and wheat germ agglutinin were effective in inhibiting the growth of Sindbis virus and vaccinia virus in chick embryo and Vero cells. They also reported that soybean agglutinin and pokeweed mitogen had little effect on the viruses.

Stitz et al in J. Gen. Virol. 34: 523–530 (1977) reported studies of the effect of Concanavalin A on the final stages of replication of fowl plague virus and Newcastle disease virus.

They suggested that a lattice was formed comprising virus particles and Concanavalin A molecules which prevented release of virions.

Cartwright in J. Gen. Virol. 34: 249–256 (1977) concluded that the effect of Concanavalin A in preventing the replication of mature vesicular stomatitis virus was due to blockage of the glycoprotein receptor sites on the cell by the lectin.

Ito et al in Arch. Virol. 57: 97–105 (1978) report that human cytomegalovirus (a herpesvirus) can be inactivated by phytohaemagglutinin whereas herpes simplex virus is not and that wheat germ agglutinin and pokeweed mitrogen were ineffective against both viruses.

Urade et al in the Arch. virol. 56: 359–363 (1978) reported that the infectivity of wild type rubella viruses was destroyed by Concanavalin A whereas this lectin had little effect on rubella pi variants. The authors concluded that the difference resulted from a difference in carbohydrate content in the structure of the envelopes.

Delagneau et al reported in Ann. Virol. (Inst. Pasteur) 132 E.: 461–471 (1981) that certain lectins, phytohaemagglutinin-Els, wheat germ agglutinin, *Ricinus communis agglutinins*, Lens culinaris agglutinin and to a lesser extent Concanavalin A, form aggregates in vitro with rabies virus, whereas limulin had no such effect. Arachis hypogaealectin was only effective in causing agglutination if the virus particles were desialated.

Ziegler and Pozos reported in Infect. Immunity 34: 588–595 (1981) that Concanavalin A binds to the herpes simplex virus and renders it inactive. A similar report with respect to succinyl Concanavalin A was published by Garrity et al. in Antimicrob. Agents Chemotherapy 21: 450–455 (1982).

Olofsson et al in Arch. virol 76: 25–28 (1983) suggested that the affinity of herpes simplex virus glycoprotein for Helix pomatia lectin was due to the presence of N-acetyl galactosamine as terminal sugar in the oligosaccharide of the virion envelope.

Klein's U.S. Pat. No. 4,197,294 disclosed the feeding of vegetable materials, including elderberries and elderflowers of an unspecified species to chickens to increase the iodine, niacin hormones, calcium and magnesium in their diets. There is no disclosure of the presence or use of a lectin.

Sugimoto's U.S. Pat. No. 4,296,025 disclosed the use of a toxic lectin (phytohaemagglutinin) in the laboratory production of interferon.

Yoshii Chemical Abstracts Vol. 49 8402 (e) discusses the reaction of leaf press juices of various plants on a nonenveloped virus (tobacco mosaic virus). Juice from inter alia *Sambucus sieboldiana* was found to have a powerful inhibitious effect on tobacco mosaic virus infection.

Furassawa in Chemical Abstracts Vol. 74 86207k disclosed the activity of alkaloids derived from bulbs of *Narcissus tazetta* and from *Sambucus sieboldiana* against certain viruses. The present invention uses lectins which are glycoproteins, not alkaloids. Alkaloids are generally toxic and not suitable for pharmaceutical use. Those of sambucus plants are found in inedible parts of the plant.

Without wishing to be bound by any theory, we believe that the lectins bind themselves to the virions thereby resulting in agglutination of virus articles which prevent their penetration to cells. It is, however, possible that alternative mechanisms are involved, for example, that the lectins bind to the cell surface thereby blocking virus receptor sites on the cell wall, or that by modifying the surface of the cell wall the lectins act to lock virus into the cell membrane, thereby preventing the release of viral replicates. It is even possible that lectins act in same way to interfere with the intracellular replication of viruses.

The applicant believes it possible that the mode of action of certain traditional herbal or fruit-based remedies from various disorders such as the common cold may have been through lectins.

One purpose of the present invention is to use non-toxic lectins for prevention or treatment of diseases caused by enveloped viruses.

Another purpose of the invention is to provide a pharmaceutical basis and mechanism for the antiviral activity.

Pharmaceutical regimen plant extracts containing some of the lectins to be used in the present invention may have previously found medical use. For example, *Sambucus nigra* has been used as a diaphoretic, a diuretic and a cathartic agent; *Datura stramonium* has been used as agent against coughs and laryngitis; Phytolacca has been used as an antirheumatic preparation and as a topical antiparasitic agent. Solanum tuberosum has been used as a spasmolytic agent. We have further identified the composition of the active components of *Sambucus nigra* 1 agglutinin.

SUMMARY OF THE INVENTION

Accordingly, in the first place, the present invention provides a method for treatment or prophylaxis for animals and man susceptible to diseases induced by enveloped viruses which comprises administration of a virus-inhibiting dose of a non-toxic lectin in the form of a pharmaceutical composition to said animals or man.

In the second place, the invention consists of a pharmaceutical composition comprising a virus inhibiting concentration of a non-toxic lectin and a pharmaceutically acceptable carrier, diluent, encapsulating agent or solvent.

From a further aspect, the invention provides an anti-viral composition comprising a lectin containing as grams aminoacid per 100 grams of polypeptide:

| | |
|---|---|
| Aspartic acid | about 16.3 |
| Threonine | about 6.8 |
| Serine | about 7.0 |
| Glutamic acid | about 11.8 |
| Proline | about 3.8 |
| Glycine | about 4.5 |
| Alanine | about 3.1 |
| Half-cystine | about 2.9 |
| Valine | about 6.0 |
| Methionine | about 3.1 |
| Isoleucine | about 8.0 |
| Leucine | about 7.7 |
| Tyrosine | about 2.7 |
| Phenylalanine | about 3.3 |
| Histidine | about 0.4 |
| Lysine | about 1.8 |
| Arginine | about 5.4 |

DETAILED DESCRIPTION OF THE INVENTION

Non-toxic lectins for use in the composition and regimens proposed in the present invention are those lectins which are non-toxic, when administered intravenously to experimental animals at doses required for effective inhibition of viral infections. Such lectins, to be used in the proposed forms and dosages, include *Sambucus nigra agglutinin* I and II, *Sambucus racemosa, Sambucus ebulus, Agaricus bisporus, Anguilla anguilla, Arachis hypogaea, Bandeiraea simplicifolia* I, II, *Bauhinia purpurea, Cytisus sessilifolius, Datura stamonium, Erythrina crist galli, Euonymus europeus, Helix aspersa, Helix pomatia, Iberis amara, Laburnum alpinum, Lens culinaris, Limax flavus, Limulus polyphemus, Lotus tetragonolubus, Maclura pomifera, Mangifera indica, Perseau americana, Phytolacca americana, Pisum sativum, Robinia pseudoacacia, Salvia horminum, Salvia sclarea, Sarothamnus scoparius, Solanum tuberosum, Sophora japonica, Trichosanthes kinlowii, Triticum vulgaris, Ulex europaeus* I, II, *Vicia faba, Vicia graminea, Vicia villosa, Wisteria floribunda, Codium fragile, Lycopersicon esculentum, Mycoplasma gallisepticum, Pelvetia canaliculata, Ptilota plumosa, Tetragonolobus purpureas* (asparagus pea, winged pea, *Lotus tetragonolobus*).

With the exception of the *Sambucus lectins,* all these lectins are commercially available for research purposes from Medac Laboratory of Hamburg, West Germany and/or from Sigma Chemicals of St. Louis, USA.

Lectins which are not commercially available may be obtained by standard extractive procedures. Lectins can be purified from saline extracts of plants by conventional techniques for protein purification such as salt precipitation, gel chromatography, ion exchange chromatography, preparative electrophoresis and related techniques. Based on the ability of lectins to specifically and reversibly bind saccharides, the affinity chromatography can be used for lectin purification, since the experimental conditions are mild and cause only little, if any, damage to the lectin. For example, *Sambucus nigra agglutinins* I and II may be obtained from elderberries by affinity chromatography on Sepharose-galactose column.

For example, elderberries from *Sambucus nigra* I may be pressed without crushing the seeds and the extract recovered by centrifugation and filtration. The extract should then be ultra-centrifuged. The lectins may be recovered from the extract by affinity chromatography on a Sepharose-galactose column followed by elution with lactose solution (e.g. 0.2M lactose solution). The lactose may be removed (for example, by passage through a Sephadex G25 column). The desorbed material is then resubjected to affinity chromatography on a Sepharose-galactose column. The first two peaks recovered during desorption are dialyzed against water and lyophilized. The first peak comprises *Sambucus nigra* II lectin which is not appreciably adsorbed on to the Sepharose-galactose column and the second peak comprises *Sambucus nigra* I lectin.

Sambucus nigra agglutinin I is a monomeric glycoprotein with an apparent molecular weight of 40,000 and consists of four isoforms with isoelectric points in the interval 4.25–4.55. It agglutinates untreated human erythrocytes of all blood groups as well as rabbit, chicken and guinea-pig blood cells, the agglutination is inhibited by D-galactose and various galactosides. The best inhibitors are N-acetylgalactosamine and thiodigalactoside.

*Sambucus nigra agglutinin* II has a molecular weight of 83,000 in its native form and about 40,000 when reduced. It is inhibited by various D galactosides. The best inhibitor is N-acetyl galactosamine. The affinity of *Sambucus nigra agglutinin* I for galactose is about 40 times higher than the affinity of *Sambucus nigra agglutinin* II for this sugar and therefore the agglutinins can be separated by affinity on a galactose-Sepharose column.

It was determined that the composition of the (*Sambucus nigra agglutinin* I lectin) had the following amino acid composition in grams per 100 grams of polypeptide:

|   |   |
|---|---|
| Aspartic acid | 16.3 |
| Threonine | 6.8 |
| Serine | 7.0 |
| Glutamic acid | 11.8 |
| Proline | 3.8 |
| Glycine | 4.5 |
| Alanine | 3.1 |
| Half-cystine | 2.9 |
| Valine | 6.0 |
| Methionine | 3.1 |
| Isoleucine | 8.0 |
| Leucine | 7.7 |
| Tyrosine | 2.7 |

-continued

|   |   |
|---|---|
| Phenylalanine | 3.3 |
| Histidine | 0.4 |
| Lysine | 1.8 |
| Arginine | 5.4 |

The composition of *Sambucus nigra agglutinin* II had the following amino acid composition per 100 grams polypeptide:

|   |   |
|---|---|
| Aspartic acid | 12.6 |
| Threonine | 7.9 |
| Serine | 6.9 |
| Glutamic acid | 12.0 |
| Proline | 4.4 |
| Glycine | 4.1 |
| Alanine | 3.5 |
| Half-cystine | 2.2 |
| Valine | 9.1 |
| Methionine | 1.6 |
| Isoleucine | 5.4 |
| Leucine | 10.1 |
| Tyrosine | 4.7 |
| Phenylalanine | 4.7 |
| Histidine | 1.0 |
| Lysine | 2.5 |
| Arginine | 7.6 |
| Tryptophan | n.d. |

Purifications of the peanut lectin (*Arachis hypogaea*) and of the soybean lectin were performed by affinity chromatography on Sepharose-$\xi$-aminocaproyl, $\beta$-D-galactopyranosylamine. *Solanum tuberosum agglutinin* is extracted from potato tubers by chromatography on G 100 Sephadex column.

It is not necessary that the lectin be isolated in absolutaly pure state, although this is often desirable for detailed pharmacokinetic studies.

The formulation and administration of drugs containing lectins will take into account the inactivation of the lectin by sugars or carbohydrate containing substances. Preparations with *Sambucus nigra* I should not contain galactose, lactose or milibiose and should not be administered either with dairy products or honey. During the drug processing the temperature should not exceed 70° C. since some lectins are destroyed by heat at that level.

The lectins may be administered in any convenient form, route and mode of entry depending upon nature of the virus to be tackled. For example, an ointment or solution for topical application may be of use in treating an ocular or genital herpes infection whereas a nose and throat spray will be of most use in treating influenza. It will be recalled that many viruses replicate only in selective tissues.

If the lectins are applied in the vicinity of the tissue in which replication occurs, there may be no need for systemic treatment. In the case of influenza virus, the primary source of infection is the mucosa of the respiratory tract, hence control of replication of the virus there can bring fast relief to the patient. On the other hand, systemic therapy will often be required. Lectins may be administered in any convenient form. In many cases, it will be convenient to administer the lectin orally or parenterally in liquid composition. Formulations containing 0.2 mg/ml up to 20 mg/ml lectin may be employed.

Typically, the patient will be given a dosage of 0.02 to 1 g daily.

In the case where a liquid formulation is intended for topical use, (i.e. in the treatment of herpes infection of the eye) the formulation may have to meet other requirements. For example, a solution for ocular use should be isotonic with eye fluids, non-irritating to the eye and sterile.

Liquid formulations may be prepared for administration in any convenient manner. In the case of formulations for parenteral administration, a solution of the lectin will be supplied in the form of a single or multiple-dose vial or ampule. Vehicles suitable for parenteral injection may be either aqueous or non-aqueous such as fixed oils of vegetable origin (cotton seed, peanut oil, corn, sesame), dimethylsulfoxide and other non-aqueous vehicles which will not interfere with therapeutic efficiency of the preparation and are nontoxic in the volume or proportion used.

In the case of solid formulations, tablets are normally formed by mixing the lectin with a binder and a diluent such as lactose or starch. In the case of lectin with affinity for lactose, the use of lactose as adjuvant in the preparation of tablets must be avoided. If the lectin is destroyed or inactivated by the gastric juice or if it may irritate the gastric mucosa, it may be desirable to provide the tablet with an enteric coating. On the other hand, if the purpose of administering the lectin is to deal with viruses present in the gastro-intestinal tract such a coating will not be provided.

A lectin-containing tablet will contain 0.02–0.2 g of lectin, together with pharmaceutically-acceptable binders or carriers. The concentration of lectin in the tablet will constitute 20–99% of the tablet weight.

Lectins may also be administered as capsules. In this case, the lectin may be combined with a diluent or carrier as described above, but no binder will be used and the mix will not be subjected to a tableting step. Dosage unit amounts of the lectin/carrier mixtures, or, if appropriate, the lectin will be encapsulated in gelatin or a similar film-forming encapsulating agent.

It may also be desirable to provide the lectin in a prolonged release formulation wherein a capsule is provided containing a pellet of smaller capsules or particles each of which is capable of being broken down by body fluids at a different rate.

Lectin formulations for topical applications are formulated in a semi-solid material such as oleaginous ointment bases (for example, white petrolatum) oil in water or water in oil emulsions, water removable bases and water-soluble bases.

In the case of a formulation which is intended to be inhaled, it may be desirable to formulate this in a low pressure aerosol can which contains the lectin either in powdered solid form or as a suspension or dispersion. Such formulations also comprise a propellant such as fluorochloro-derivatives of methane and methane.

When used to control viral infections in domestic animals, the lectin may be incorporated into the animals' feed. For example, the lectins may be included in a premix together with various minerals or antibiotics.

In my own investigation of the effects of *Sambucus nigra agglutinin* I on viral interaction with mammalian cells, I have obtained the following results:

(1) Abrogation of cytophathic effect induced by cytomegalovirus on human lung fibroblastic monolayers was effected by *Sambucus nigra agglutinin* I at a concentration of 100 μg/ml.

(2) Immortalization of human cord blood lymphocytes induced by Epstein-Barr virus was prevented by *Sambucus nigra agglutinin* I at a concentration of 200 μg/ml.

(3) Cytopathic effect induced by herpes virus type I in human embryonic lung fibroblasts was prevented by *Sambucus nigra agglutinin* II at a concentration of 200 μg/ml.

Based on projected extrapolations, effective doses comparable for an adult should be between 0.6 and 1.2 g to reach comparable concentrations of lectin in the blood circulation.

PHARMACOLOGY TESTING

Series 1

Four groups each of 20 male C57 black mice aged 5 to 6 weeks tested. To group I there was administered intra-nasally 0.1 ml. of the suspension of virus A/PR8/34 CHON1 (an influenza virus type A) which had been cultivated in the allantonic cavity of 10–11 day old embryonated chicken eggs.

To group II there was administered a similar supension which had been incubated with 50 μg *Sambucus nigra agglutinin* I lectin.

To group III there was administered only the *Sambucus nigra agglutinin* I lectin.

Group IV was a control group to which no virus or lectin was administered.

In group I, 8 mice died 6 days after administration of the virus, 5 mice died 7 days after administration, 3 mice died after 8 days and the remaining mice died 9 days after the administration.

In group II, one mouse died after 9 days and one mouse died after 11 days. There were no other mortalities in group II.

There were no mortalities in groups III and IV.

Three weeks after administration, the surviving members of group II were sacrificed and examined. It was determined that these mice had contracted influenza but had recovered.

Series 2

IN VITRO ASSAY FOR NEUTRALIZATION OF INFLUENZA VIRUS (FOWL PLAGUE VIRUS)—INFECTIVITY BY SAMBUCUS NIGRA I LECTIN

The assay was carried out in microtiter plates containing human renal carcinoma monolayer cell cultures. The monolayers were washed. The influence of SNA I was determined by 5 minutes incubation of 0.1 ml of two-fold dilutions of the virus with 0.1 ml of a 50 μg/ml lectin solution. The assay was followed visually during the incubation at 37° C. using a phase contrast microscope. The monolayers were checked for cytopathic effect and colored with fuchsin-methylene blue when the virus controls were completely lysed. Cell controls were performed in the presence and in the absence of lectin. The number of plaque forming units in the virus suspension was determined.

The assay showed that incubation of the virus with the lectin provides an effective neutralization of the infectivity of the virus in vitro. The assay was repeated, using different conentrations of lectins and virus and the results indicate that, approximately estimated, one plaque forming unit can be neutralized by 0.5 μg/ml lectin solution.

I claim:

1. A method of treatment or prophylaxis for animals and man suffering from, or exposed to, a disease induced by an influenza virus which consists of administering a virus-inhibiting amount of a pharmaceutical composition comprising a non-toxic lectin selected from the group consisting of *Sambucus nigra agglutinin* I and *Sambucus nigra agglutinin* II to said animals or humans.

2. A method according to claim 1 wherein said non-toxic lectin is *Sambucus nigra agglutinin* I.

3. A method according to claim 1 wherein consists of administering said composition to said animal or human in an amount to supply lectin to said animal or human in an amount from 0.4 to 20 mg/kg body weight per unit dose.

4. A method according to claim 2 which consists of administering said composition to said animal or human in an amount to supply lectin to said animal or human in an amount of from 0.4 to 20 mg/kg weight per unit dose.

5. A method according to claim 3, wherein said composition is administered orally in the form of capsules or tablets or food additive comprising from 0.02 to 0.2 g lectin per unit.

6. A method according to claim 3, wherein said composition is administered to a mammal or poultry suffering from infection by or exposed to influenza virus which comprises administering a nasal spray to said mammal or poultry.

7. A method of treatment or prophylaxis for animals and man suffering from or exposed to a disease induced by an influenza virus which consists of administering a virus inhibiting amount of a pharmaceutical composition comprising a lectin containing the amino acids in the parts stated below per 100 parts by weight of polypeptide:

|  |  |
|---|---|
| Aspartic acid | about 16.3 |
| Threonine | about 6.8 |
| Serine | about 7.0 |
| Glutamic acid | about 11.8 |
| Proline | about 3.8 |
| Glycine | about 4.5 |
| Alanine | about 3.1 |
| Half-cystine | about 2.9 |
| Valine | about 6.0 |
| Methionine | about 3.1 |
| Isoleucine | about 8.0 |
| Leucine | about 7.7 |
| Tyrosine | about 2.7 |
| Phenylalanine | about 3.3 |
| Histidine | about 0.4 |
| Lysine | about 1.8 |
| Arginine | about 5.4 |

8. A method according to claim 7 which consists of administering said composition to said animal or human in an amount to supply said lectin to said animal or human in an amount from 0.4 to 20 mg/kg body weight per unit dose.

9. A method according to claim 7 wherein said composition is administered orally in the form of capsules or tablets comprising from 0.02 to 0.2 g of said lectin per unit.

10. A method according to claim 7 wherein said composition is administered as a nasal spray.

11. A pharmaceutical composition consisting of a viral replicative inhibiting concentration of a non-toxic lectin selected from the group consisting of *Sambucus nigra agglutinin* I and *Sambucus nigra agglutinin* II and a pharmaceutically-acceptable carrier, diluent, encapsulating agent or solvent.

12. A pharmaceutical composition according to claim 11 wherein the composition is liquid emulsion or suspension and comprises from 0.2 to 20 mg/ml of lectin.

13. A pharmaceutical composition according to claim 12 wherein the composition is in tablet form, each tablet comprising from 0.02 to 0.2 g of lectin.

14. A pharmaceutical composition according to claim 11 wherein the composition is in capsule form, each capsule comprising from 0.02 to 0.2 g of lectin.

15. A pharmaceutical composition according to claim 11 wherein the composition is in the form of an aerosol spray and further comprises a pharmaceutically acceptable propellant.

16. A pharmaceutical composition according to claim 11 which is in the form of an ointment or a paste or a solution.

17. A pharmaceutical composition consisting of a viral replicative inhibiting concentration of a lectin containing per 100 parts by weight of polypeptide the following amino acids in the stated parts by weight:

|  |  |
|---|---|
| Aspartic acid | about 16.3 |
| Threonine | about 6.8 |
| Serine | about 7.0 |
| Glutamic acid | about 11.8 |
| Proline | about 3.8 |
| Glycine | about 4.5 |
| Alanine | about 3.1 |
| Half-cystine | about 2.9 |
| Valine | about 6.0 |
| Methionine | about 3.1 |
| Isoleucine | about 8.0 |
| Leucine | about 7.7 |
| Tyrosine | about 2.7 |
| Phenylalanine | about 3.3 |
| Histidine | about 0.4 |
| Lysine | about 1.8 |
| Arginine | about 5.4 | and a pharmaceutically-acceptable carrier, diluent, encapsulating agent or solvent.

18. A pharmaceutical composition according to claim 17 wherein said composition is in tablet or capsule form, each tablet or capsule comprising 0.02 to 0.2 g of said lectin.

19. A pharmaceutical composition according to claim 17 in the form of an aerosol spray and further comprising a pharmaceutically-acceptable propellant.

20. A pharmaceutical composition according to claim 17 which is in the form of an ointment, paste or solution.

21. A method according to claim 1, wherein said lectin is applied topically.

* * * * *